United States Patent
Strubel et al.

(10) Patent No.: US 12,191,129 B2
(45) Date of Patent: *Jan. 7, 2025

(54) METHOD FOR IDENTIFYING MICROORGANISMS BY MASS SPECTROMETRY

(71) Applicant: BIOMERIEUX, INC., Durham, NC (US)

(72) Inventors: Grégory Strubel, Manosque (FR); Maud Arsac, Saint Chamond (FR); Denis Desseree, Montluel (FR); Pierre-Jean Cotte-Pattat, Lagnieu (FR)

(73) Assignee: BIOMERIEUX, INC., Durham, NC (US)

(*) Notice: Subject to any disclaimer, the term of this patent is extended or adjusted under 35 U.S.C. 154(b) by 1336 days.

This patent is subject to a terminal disclaimer.

(21) Appl. No.: 16/708,419

(22) Filed: Dec. 9, 2019

(65) Prior Publication Data

US 2020/0111653 A1 Apr. 9, 2020

Related U.S. Application Data

(63) Continuation of application No. 14/361,794, filed as application No. PCT/IB2012/056860 on Nov. 30, 2012, now Pat. No. 10,541,119.

(30) Foreign Application Priority Data

Dec. 2, 2011 (EP) .................................. 11306610

(51) Int. Cl.
*H01J 49/00* (2006.01)
*G01N 33/68* (2006.01)
(Continued)

(52) U.S. Cl.
CPC ...... *H01J 49/0036* (2013.01); *G01N 33/6848* (2013.01); *G16B 40/10* (2019.02); *G16B 99/00* (2019.02)

(58) Field of Classification Search
CPC . H01J 49/0036; G01N 33/6848; G16B 40/10; G16B 99/00
See application file for complete search history.

(56) References Cited

U.S. PATENT DOCUMENTS

| 4,008,388 A | 2/1977 | McLafferty et al. |
| 2004/0195500 A1 | 10/2004 | Sachs et al. |

(Continued)

FOREIGN PATENT DOCUMENTS

| CN | 102253110 A | 11/2011 |
| CN | 102253111 A | 11/2011 |

(Continued)

OTHER PUBLICATIONS

International Search Report mailed Apr. 23, 2013 in corresponding application No. PCT/IB2012/056860 of parent U.S. Appl. No. 14/361,794 (3 pages).

(Continued)

*Primary Examiner* — Larry D Riggs, II
*Assistant Examiner* — Guozhen Liu
(74) *Attorney, Agent, or Firm* — Seckel IP, PLLC

(57) ABSTRACT

A method of identifying a microorganism by mass spectrometry, including acquiring at least one mass spectrum of said microorganism; for each acquired mass spectrum: detecting peaks of the spectrum in a predetermined mass range; generating a list of peaks identifying at most one peak in each interval of a predetermined subdivision of the range of mass-to-charge ratios, the width of the intervals of the subdivision logarithmically increasing along with the mass-to-charge ratio, and analyzing the list(s) of peaks obtained (Continued)

according to a knowledge base of previously-identified microorganisms and/or types of microorganisms.

20 Claims, 2 Drawing Sheets

Related U.S. Application Data

(60) Provisional application No. 61/566,025, filed on Dec. 2, 2011.

(51) Int. Cl.
*G16B 40/10* (2019.01)
*G16B 99/00* (2019.01)

(56) References Cited

U.S. PATENT DOCUMENTS

| | | |
|---|---|---|
| 2008/0029697 A1 | 2/2008 | Willis et al. |
| 2009/0055101 A1 | 2/2009 | Strubel et al. |
| 2010/0116980 A1 | 5/2010 | Nassif et al. |
| 2011/0202282 A1 | 8/2011 | Kostrzewa |

FOREIGN PATENT DOCUMENTS

| | | |
|---|---|---|
| EP | 2786397 B1 | 10/2019 |
| JP | 2006-522340 A | 9/2006 |
| JP | 2007-316063 A | 12/2007 |
| JP | 2010-515915 A | 5/2010 |
| WO | 2004089972 A2 | 10/2004 |
| WO | 2008084409 A2 | 7/2008 |

OTHER PUBLICATIONS

Lay, "Maldi-tof spectrometry of bacteria", Mass Spectrometry Reviews, 2001, vol. 20, No. 4, pp. 172-194 (1-page abstract only).
Russell, "Microorganism Characterization by Single Particle Mass Spectrometry", Mass Spectrometry Reviews, 2009, vol. 28, pp. 376-387 (cited in ISR in parent).
Hettick et al., "Proteomic Profiling of Intact Mycobacteria by Matrix-Assisted Laser Desorption/Ionization Time-of-Flight Mass Spectrometry", Anal. Chem., 2004, vol. 76, No. 19, pp. 5769-5776 (cited in ISR in parent).
Drancourt, "Detection of microorganisms in blood specimens using matrix-assisted laser desroption ionization time-of-flight mass spectrometry: a review", Clin. Microbiol. Infect., 2010, vol. 16, pp. 1620-1625.
De Bruyne et al., "Bacterial species identification from MALDI-TOF mass spectra through data analysis and machine earning", Systematic and Applied Microbiology, 2011, vol. 34, pp. 20-29.
Han et al., "Data Preprocessing", Chapter 2, "Data Mining: Concepts and Techniques", 2nd. Ed., Elsevier Science & Technology, Burlington, MA (USA), pp. 47-103.
Barbarini et al., "A New Approach for the Analysis of Mass Spectrometry Data for Biomarker Discovery", AMIA 2006 Symposium Proceedings, 2006, pp. 26-30.
Listgarten et al., "Satistical and Computational Methods for Comparative Proteomic Profiling Using Liquid Chromatography-Tandem Mass Spectrometry", Molecular & Cellular Proteomics, 2005, vol. 4.4, pp. 419-434.
Chinese Office Action and Search Report dated Oct. 20, 2015 in corresponding Chinese application No. 201280058472 of parent U.S. Appl. No. 14/361,794; with English machine translation (12 pages) (D3/D6 US20040195500, D4 U.S. Pat. No. 4,008,388 and D5 US20080029697 cited in the Chinese search report are not listed in this IDS form since they are listed in another IDS form filed concurrently).
Japanese Search Report dated May 16, 2016 in corresponding Japanese application No. 201544031 of parent U.S. Appl. No. 14/361,794; with English machine translation (27 pages) (D1 De Bruyne et al., Syst. and Appl. Microbiol. 2011, 34, 20-29 and D3 US20040195500 cited in the Japanese search report are not listed in this IDS form since they are listed in other IDS forms filed concurrently).
European Search Report dated Feb. 7, 2020 in related divisional application No. EP19199848.3 (with English translation; total 18 pages) (D1, and D3-D6 cited in the ESR are not listed in this IDS since they were already listed in the IDS filed Dec. 9, 2019).
Keys et al., "Compilation of a MALDI-TOF mass spectral database for the rapid screening and characterisation of bacteria implicated in human infectious diseases", Infection Genetics and Evolution, Elsevier, Amsterdam, The Netherlands, 2004, vol. 4, No. 3, pp. 221-242 (in English) (D2 cited in the ESR).

METHOD FOR IDENTIFYING MICROORGANISMS BY MASS SPECTROMETRY

CROSS-REFERENCE TO RELATED APPLICATIONS

This application is a continuation of U.S. application Ser. No. 14/361,794, which is a U.S. national stage of PCT/IB2012/056860 filed Nov. 30, 2012 and which is hereby incorporated by reference herein in its entirety, and each of them claims the benefit of U.S. provisional application No. 61/566,025 filed Dec. 2, 2011.

FIELD OF THE INVENTION

The invention relates to the identification of microorganisms, and particularly bacteria, by mass spectrometry.

BACKGROUND OF THE INVENTION

It is known to use mass spectrometry to identify microorganisms, and more particularly bacteria. A sample of the microorganism is prepared, after which a mass spectrum of the sample is acquired and pre-processed: spectrum denoising (noise removal), filtering of the background noise (imputable to the detector). The significant peaks of the pre-processed spectrum are then detected and the list of peaks thus obtained is "analyzed" and "compared" with data of a knowledge base built from lists of typical peaks of an identified microorganism or group of microorganisms (strain, genus, family, etc.).

Although this principle seems simple offhand, its implementation is however delicate. Indeed, first, the quantity of information contained in a mass spectrum, and particularly the number of peaks, is very large, which requires very powerful calculation tools to create a robust knowledge base, as well as to implement classification, comparison, and decision algorithms.

There then is a high measurement uncertainty, particularly as concerns the location of speaks in the spectrum. It can indeed be observed that from one measurement to the other on a same spectrometer, as well as from one spectrometer to the other, a peak representing a given molecule does not have a fixed position in the measured spectrums, or at the very least the peak is not contained in a range. Thus, a peak of an acquired spectrum and corresponding to a given protein molecule cannot be identified as corresponding to said protein molecule by the classification algorithm. Finally, this uncertainty is not constant over the range of mass-to-charge ratios and increases as this ratio increases.

SUMMARY OF THE INVENTION

The invention aims at providing a method enabling to robustly identify microorganisms by mass spectrometry due to a decrease in the mass of information to be analyzed and a decrease in the impact of the lack of accuracy as to the location of mass spectrum peaks.

For this purpose, an object of the invention is a method of identifying a microorganism by mass spectrometry, comprising:
acquiring at least one mass spectrum of said microorganism;
for each acquired mass spectrum:
detecting peaks of the spectrum in a predetermined mass range;
generating a list of peaks identifying at most one peak in each interval of a predetermined subdivision of the range of mass-to-charge ratios, the width of the intervals of the subdivision increasing along with the mass-to-charge ratio according to relations:

$$L(b) = \exp\left(\frac{b-\beta}{\alpha}\right) \times \left(\exp\left(\frac{1}{\alpha}\right) - 1\right)$$

$$\alpha = \frac{b_{min} - (b_{max} + 1)}{\ln m_{min} - \ln m_{max}}$$

$$\beta = \frac{(b_{max} + 1) \times \ln m_{min} - b_{min} \times \ln m_{max}}{\ln m_{min} - \ln m_{max}}$$

where the subdivision intervals are referenced with integers greater than 1 from integer $b_{min}$, for the lowest mass-to-charge ratios in the range, to integer $b_{max}$, for the highest mass-to-charge ratios in the range, L(b) is the width of the interval referenced with integer b, $m_{min}$ is a lower bound of the range of mass-to-charge ratios, and $m_{max}$ is an upper bound of the range of mass-to-charge ratios; and
analyzing the list(s) of peaks obtained according to the knowledge base of previously-identified microorganisms and/or types of microorganisms.

In other words, the continuous space of mass-to-charge ratios, or Thomsons space, is log-arithmically quantized, and a single peak is retained in each quantization interval if several peaks are present in this interval. This enables to substantially decrease the amount of data to be processed. Further, the accurate position of a peak is replaced with the reference of the interval to which the peak belongs. This decreases the measurement uncertainty relative to the position of peaks since it is no longer needed to compare an accurate position with the knowledge base. It is rather determined whether the peak belongs to an interval. Finally, the logarithmic progression of the interval width enables to adapt to the fact that the instrument has a constant relative accuracy:

$$p = \frac{\Delta \mu}{m} = \text{constant}$$

According to an embodiment, the predetermined range of Thomsons is between 3,000 Thomsons and 17,000 Thomsons. The inventors have indeed observed that this range is sufficient for the identification of most bacteria and yeast/mould. It can especially be observed that local peaks under 3,000 Thomsons are common to many microorganisms and are thus not discriminating.

According to an embodiment, there are from 900 to 1,500 intervals, particularly from 1,200 to 1,400. The inventors have observed that these intervals form the optimal compromise between the loss of information induced by the quantization of the Thomsons space and the accuracy gained by the replacing of the accurate peak position with intervals.

According to an embodiment, the peak kept in an interval of the subdivision is the peak having the highest intensity. Other choices are however possible. For example, it is possible to select the average value or the median value of the intensities of the peaks present in the interval.

According to an embodiment, the mass spectrometry is a MALDI-TOF spectrometry.

Another object of the invention is a method of identifying a microorganism by mass spectrometry, comprising:
- a mass spectrometer capable of generating mass spectrums of microorganisms to be identified;
- a calculation unit capable of identifying the microorganisms associated with the mass spectrums generated by the spectrometer by implementing the method of any of the foregoing claims.

BRIEF DESCRIPTION OF THE DRAWINGS

The invention will be better understood on reading of the following description provided as an example only in relation with the accompanying drawings, where.

DETAILED DESCRIPTION OF THE INVENTION

Figure 1:
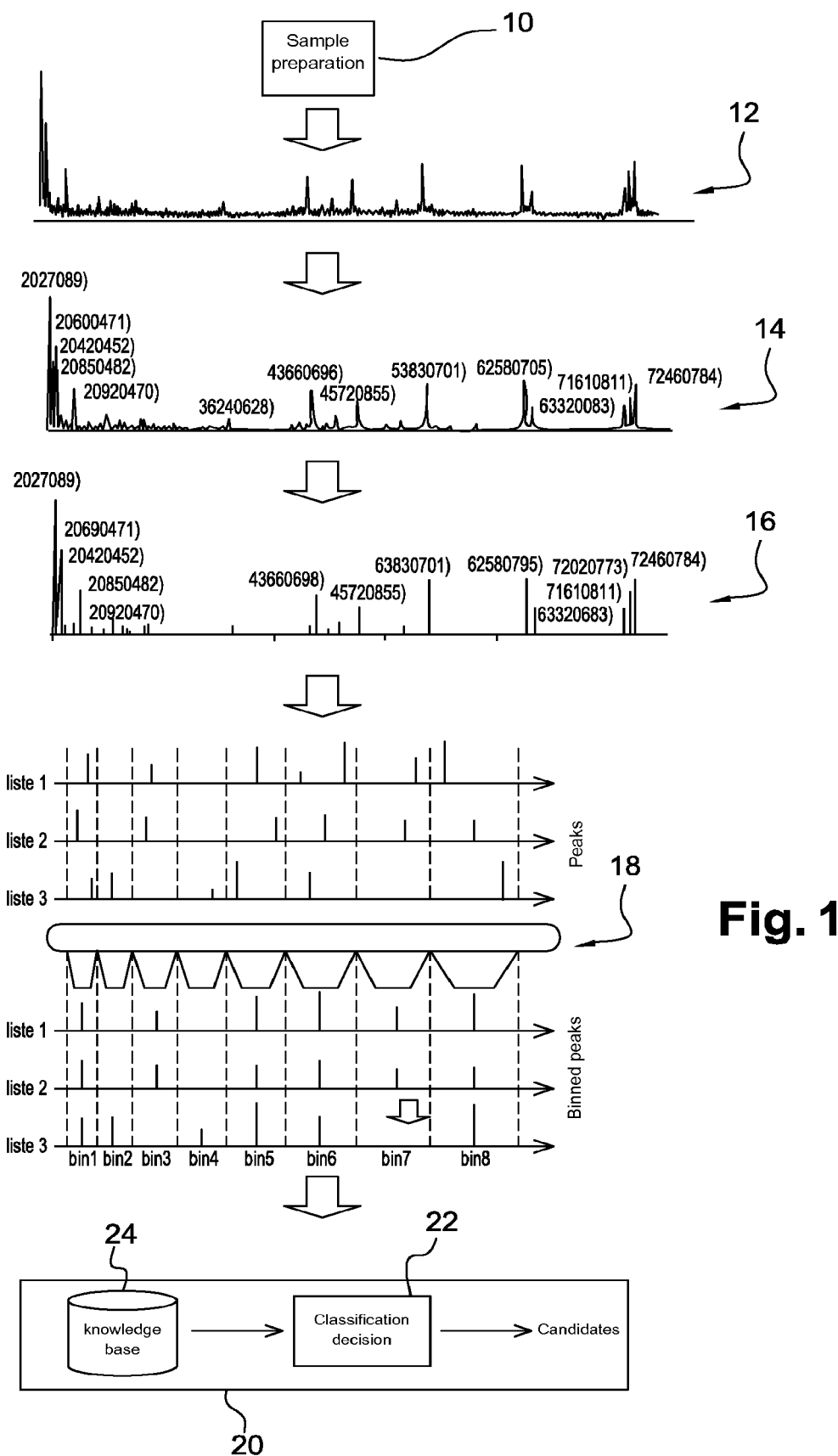
FIG. 1 is a flowchart of the method according to the invention.

Referring to FIG. 1, a method according to the invention of bacteria identification by means of MALDI-TOF type (acronym for "Matrix-assisted laser desorption/ionization time of flight") mass spectrometry will now be described.

The method begins with the preparation, at step 10, of a sample of a bacterium to be identified, followed by the acquisition, at step 12, of one or a plurality of mass spectrums of the sample prepared by means of a MALDI-TOF type mass spectrometry. MALDI-TOF mass spectrometry is well known per se and will not be described in further detail hereafter. Reference may for example be made to Jackson O. Lay's document, "*Maldi-tof spectrometry of bacteria*", Mass Spectrometry Reviews, 2001, 20, 172-194.

The method carries on, at step 14, with the pre-processing of the acquired spectrums, particularly to denoise and smooth the spectrums. More particularly, the spectrum base line, which represents the spectrometer background noise, is removed.

An identification of the peaks present in the acquired spectrums is then performed at step 16, for example, by means of a peak detection algorithm, for example based on the detection of local maximum points. A list of peaks for each spectrum, comprising the location and the intensity of the spectrum peaks, is thus generated.

Advantageously, the peaks are identified in limited Thomsons range $[m_{min}; m_{max}]$, preferably Thomsons range $[m_{min}; m_{max}] = [3,000; 17,000]$. Indeed, it has been observed that the information sufficient to identify the microorganisms is contained in this range, and that it is thus not needed to take a wider range into account.

The method carries on at step 18, by a quantization or "binning" step. To achieve this:
range $[m_{min}; m_{max}]$ is divided into intervals having a width logarithmically increasing along with the Thomsons according to relation:

$$L(b) = \exp\left(\frac{b-\beta}{\alpha}\right) \times \left(\exp\left(\frac{1}{\alpha}\right) - 1\right) \quad (1)$$

$$\alpha = \frac{b_{min} - (b_{max}+1)}{\ln m_{min} - \ln m_{max}} \quad (2)$$

$$\beta = \frac{(b_{max}+1) \times \ln m_{min} - b_{min} \times \ln m_{max}}{\ln m_{min} - \ln m_{max}} \quad (3)$$

where the subdivision intervals are referenced with integers greater than 1, from integer $b_{min}$, for example, equal to 1, to integer $b_{max}$ and $L(b)$ is the width of the interval referenced with integer b. Integer $b_{min}$ corresponds to the interval of the lowest mass-to-charge ratios in range $[m_{min}; m_{max}]$, and integer $b_{max}$ corresponds to the interval of the highest mass-to-charge ratios in range $[m_{min}; m_{max}]$. The Thomsons axis is thus quantized according to relation:

$$b(m) = \lfloor \alpha \ln m + \beta \rfloor$$

where $\lfloor \ \rfloor$ symbolizes a rounding to the next lower integer value;

for each interval comprising a plurality of peaks, a single peak is kept, advantageously the peak having the highest intensity. A vector is thus generated for each measured spectrum. Each component of the vector corresponds to a quantization interval and has as a value the intensity of the peak kept for this interval, value "0" meaning that no peak has been detected in the interval.

For example, at step 18 of the drawing in FIG. 1, three lists of identified peaks are illustrated, that is, "list 1", "list 2", and "list 3", each corresponding to a measured mass spectrum. The Thomsons space is divided into 8 intervals, from "bin1" to "bin8", having a logarithmically increasing width, and only the peak having the highest intensity is kept in each interval. Thus, for interval "bin6" of first list "list 1", one peak is eliminated. For lists "list 1", "list 2", and "list 3", the following matrix is for example obtained, each line corresponding to a list:

$$\begin{pmatrix} 900 & 0 & 98 & 0 & 1{,}300 & 1{,}556 & 400 & 2{,}000 \\ 505 & 700 & 200 & 0 & 500 & 200 & 345 & 256 \\ 700 & 0 & 0 & 100 & 2{,}340 & 1{,}786 & 0 & 2{,}507 \end{pmatrix}$$

It can thus be shown that by means of a quantization such as described hereabove, the increase of the uncertainty as to the position of the peaks as masses increase is taken into account. Particularly, the subdivision according to the invention of the Thomsons axis enables to take into account an uncertainty of the following type:

$$p = \frac{\Delta\mu}{m} \quad (4)$$

where p is the accuracy of the location of a peak, $\Delta\mu$ is the uncertainty of measurement of the position of the spectrometer peaks, and m is the real position of the peak. The quantization thus is an adaptive quantization which takes into account the measurement error of the mass spectrometer.

The replacing of the measured location of a peak with the reference to the interval to which it belongs is equivalent to aligning the position of the peak on the middle of the interval. It can be verified that the logarithmic subdivision according to the invention enables to decrease the uncertainty according to relation (4). Indeed:

$$\frac{L(b)}{m_{bar}(b)} = \frac{2\left(\exp\left\{\frac{1}{\alpha}\right\} - 1\right)}{\left(\exp\left\{\frac{1}{\alpha}\right\} + 1\right)} = ct$$

where $m_{bar}(b)$ is the middle of the interval referenced with reference b.

The intensity of a peak is highly variable from one spectrum to another and/or from one spectrometer to another. Du to this variability, it is very difficult to take into account raw intensity values. Advantageously, though optionally, the method carries on with an intensity discretization step. This step may for example comprise a simple "binarization" (presence/absence).

Thus, each line of the matrix is "binarized" and then normalized, the matrix thus identifying for each acquired spectrum the presence or the absence of a peak in the intervals. For example, the previous matrix is binarized into matrix:

$$\begin{pmatrix} 1 & 0 & 1 & 0 & 1 & 1 & 1 & 1 \\ 1 & 1 & 1 & 0 & 1 & 1 & 1 & 1 \\ 1 & 0 & 0 & 1 & 1 & 1 & 0 & 1 \end{pmatrix}$$

The inventors have further noted that the information relevant to identify a bacterium is essentially contained in the absence and/or the presence of peaks, and that the intensity information is less relevant, particularly due to its high variability. Thus, for example, it is possible to identify bacteria based on this type of lists by means of usual classification tools such as logistic regression, discriminant analysis, classification trees, LASSO methods, SVM-type algorithms (acronym for "support vector machine"). The matrix thus binarized may be used in all known classification tools.

The method then caries on, at step 20, with the analysis of the matrix obtained at the previous step. More particularly, a classification and decision algorithm 22 is implemented according to a knowledge base 24 built according to lists of peaks of previously-identified microorganisms and/or microorganism types. One or several candidates, or a type of microorganisms (family, germ, species, sub-species) are thus identified for the analyzed sample.

The method according to the invention thus enables to reduce a list of peaks of variable size and of continuous values along 2 axes (m/z, intensities) to a vector of reasonable fixed size.

Knowledge base 24 is built from lists of peaks generated as described hereabove and associated with previously-identified microorganisms and/or microorganism types. It should be understood that the invention applies to any type of classification algorithm and of knowledge base. The quantization according to the invention particularly enables to decrease the amount of data, as well as to eliminate problems of peak location accuracy, and thus enables to construct a more robust knowledge base, and this, in a simpler way. The implementation is much simpler than the calculation of a tolerant distance (for example) and allows an almost fully automated building of the knowledge base.

Figure 2:
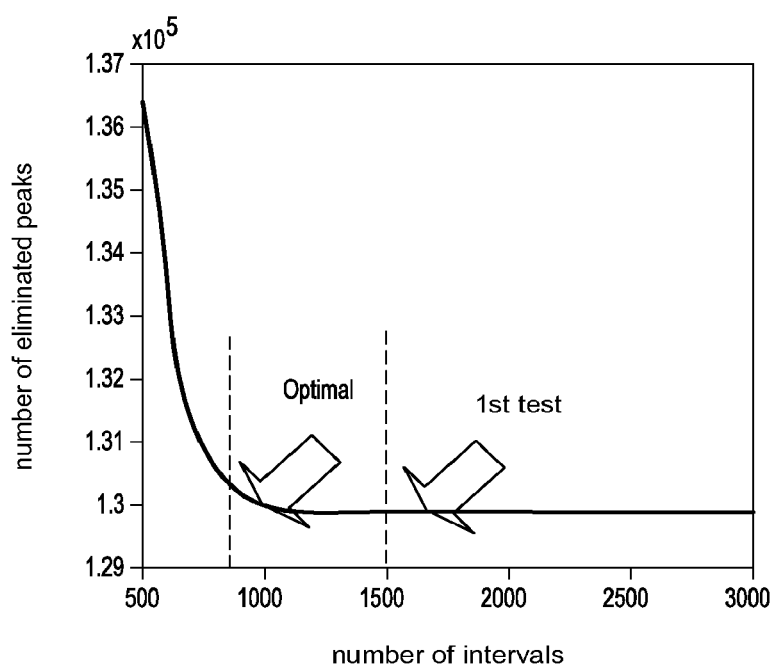
FIG. 2 is a plot of the number of peaks eliminated from a mass spectrum according to the number of intervals of the quantization according to the invention.

The number of intervals is advantageously selected between 900 and 1,500, and preferably between 1,200 and 1,400 for the identification of microorganisms. The inventors have observed that these intervals form the optimal compromise between the loss of information induced by the quantization of the Thomsons space and the accuracy gained by the replacing of the accurate position of peaks with intervals. The inventors have carried out tests and have modeled, as illustrated in FIG. 2, the number of peaks eliminated by the quantization according to the number of intervals. It should in particular be noted that beyond a number of intervals, the decrease of the amount of data is negligible, and that under a given number, the number of eliminated peaks increases exponentially.

Comparative tests have been carried out between the logarithmic quantization of the invention and a constant quantization, that is, a quantization for which all intervals have an identical width, and this for a same mass spectrometer and an identical classification and decision algorithm and knowledge base construction. These tests are described in the following table. The error corresponds to the microorganism identification error.

| Quantization | Number of intervals | Error (%) | Occupied memory space (Mo) |
|---|---|---|---|
| logarithmic | 300 | 10.33 | 120 |
| logarithmic | 600 | 6.25 | 240 |
| logarithmic | 800 | 5.3 | 320 |
| logarithmic | 1,000 | 5.4 | 400 |
| logarithmic | 1,300 | 5.0 | 520 |
| logarithmic | 1,700 | 6.9 | 680 |
| logarithmic | 2,300 | 8.52 | 920 |
| logarithmic | 4,700 | 12.2 | 1,880 |
| constant | 300 | 12.4 | 120 |
| constant | 600 | 8.75 | 240 |
| constant | 800 | 7.2 | 320 |
| constant | 1,000 | 6.6 | 400 |
| constant | 1,300 | 6.2 | 520 |
| constant | 1,700 | 5.9 | 680 |
| constant | 2,300 | 7.22 | 920 |
| constant | 4,700 | 11.0 | 1,880 |

By selecting 1,000 intervals of constant width, the interval width is equal to the resolution of the mass spectrometer used for the tests for a mass-to-charge ratio equal to 17,000 Thomsons. By selecting 4,700 intervals of constant width, the interval width is equal to the resolution of the mass spectrometer for a mass-to-charge ratio equal to 3,000 Thomsons.

By selecting 1,700 logarithmic intervals according to relations (1) to (3), with $b_{min}=1$, the width of each interval is equal to the accuracy of the spectrometer for a mass-to-charge ratio equal to the middle of the interval. It can however be observed that in average, a number of 1,300 intervals provides both the lowest error identification rate and the smallest occupied memory space. Particularly, as compared with the number of 1,700 intervals, which at first sight seems better adapted, a gain of 2 error points (a −28% error) is obtained, while decreasing the occupied memory space, as indicated in the above table. The number of 1,300 is thus preferred to implement the invention.

It should also be noted that the quantization according to the invention provides a maximum error rate lower by at least 1 point (a −15% error) than that of a constant quantization, as well as a lower memory footprint (−25%). For small numbers of intervals, the quantization according to the invention thus provides better results than a constant quantization. This thus enables to keep a small number of intervals, even while increasing the resolution of the mass spectrometer or the retained Thomsons range $[m_{min}; m_{max}]$. It can thus be observed that for a same error rate, for example, approximately 6%, the quantization according to the invention only requires 700 intervals while the constant quantization requires 1,700.

What is claimed is:

1. A method of providing an identification decision for a microorganism using a processor-based calculation unit and a mass spectrum obtained by mass spectrometry from a mass spectrometer, comprising:
   (i) providing at least one mass spectrum of a sample of the microorganism over a predetermined range of mass-to-charge ratios, wherein said mass spectrum was generated by a mass spectrometer;
   (ii) for each of said acquired at least one mass spectrum:
      (a) detecting, using the processor of the calculation unit, peaks of the mass spectrum in the predetermined range of mass-to-charge ratios;
      (b) generating, using the processor of the calculation unit, a list of peaks in intervals of a predetermined subdivision of the predetermined range of mass-to-charge ratios, the width of the intervals of the subdivision increasing along with the mass-to-charge ratio according to relations:

$$L(b) = \exp\left(\frac{b-\beta}{\alpha}\right) \times \left(\exp\left(\frac{1}{\alpha}\right) - 1\right)$$

$$\alpha = \frac{b_{min} - (b_{max} + 1)}{\ln m_{min} - \ln m_{max}}$$

$$\beta = \frac{(b_{max} + 1) \times \ln m_{min} - b_{min} \times \ln m_{max}}{\ln m_{min} - \ln m_{max}}$$

where
the subdivision intervals are referenced with integers greater than 1, from integer $b_{min}$, for the lowest mass-to-charge ratios in the predetermined range of mass-to-charge ratios, to integer $b_{max}$, for the higher mass-to-charge ratios in the predetermined range of mass-to-charge ratios,
$L(b)$ is the width of the interval referenced with integer b,
$m_{min}$ is a lower bound of the predetermined range of mass-to-charge ratios, and
$m_{max}$ is an upper bound of the predetermined range of mass-to-charge ratios,
wherein, in the list of peaks, the processor of the calculation unit identifies at most one peak in each interval, so as to obtain a vector for each of said at least one mass spectrum,
wherein the vector(s) for the at least one mass spectrum form a matrix representative of the microorganism; and
   (iii) providing an identification decision for the microorganism to be identified by comparing the representative matrix with a knowledge base of matrices representative of previously-identified microorganisms and/or types of microorganisms, wherein said knowledge base is stored in a memory.

2. The method of claim 1, wherein the predetermined range of mass-to-charge ratios is in the range from 3,000 Thomsons to 17,000 Thomsons.

3. The method of claim 1, wherein there are from 900 to 1,500 intervals.

4. The method of claim 3, wherein there are from 1,200 to 1,400 intervals.

5. The method of claim 1, wherein the peak kept in an interval of the subdivision is a maximum peak.

6. The method of claim 1, wherein the at least one mass spectrum of the sample of the microorganism was generated using MALDI-TOF spectrometry.

7. The method of claim 1, further comprising returning an identification decision to a user.

8. The method of claim 1, further comprising generating the at least one mass spectrum of the sample of the microorganism to be identified by the mass spectrometer.

9. The method of claim 1, further comprising storing the matrix representative of the microorganism to be identified in the memory of the calculation unit.

10. The method of claim 1, wherein the matrix representative of the microorganism to be identified is in the form of a binarized matrix that identifies for each of the at least one mass spectrum the presence or absence of a peak in the intervals.

11. A device for providing an identification decision regarding a microorganism based on mass spectrum data, comprising a computer program stored in a non-transitory storage medium, wherein the computer program is adapted to implement the following instructions when the computer program is executed by a processor:
   (i) providing to the calculation unit at least one mass spectrum of a sample of a microorganism to be identified over a range of mass-to-charge ratios, wherein the mass spectrum was generated by a mass spectrometer;
   (ii) for each of said acquired at least one mass spectrum:
      (a) detecting peaks of said mass spectrum in the predetermined range of mass-to-charge ratios;
      (b) generating a list of peaks in intervals of a predetermined subdivision of the predetermined range of mass-to-charge ratios, the width of the intervals of the subdivision increasing along with the mass-to-charge ratio according to relations:

$$L(b) = \exp\left(\frac{b-\beta}{\alpha}\right) \times \left(\exp\left(\frac{1}{\alpha}\right) - 1\right)$$

$$\alpha = \frac{b_{min} - (b_{max} + 1)}{\ln m_{min} - \ln m_{max}}$$

$$\beta = \frac{(b_{max} + 1) \times \ln m_{min} - b_{min} \times \ln m_{max}}{\ln m_{min} - \ln m_{max}}$$

where
the subdivision intervals are referenced with integers greater than 1, from integer $b_{min}$, for the lowest mass-to-charge ratios in the predetermined range of mass-to-charge ratios, to integer $b_{max}$, for the higher mass-to-charge ratios in the predetermined range of mass-to-charge ratios,
$L(b)$ is the width of the interval referenced with integer b,
$m_{min}$ is a lower bound of the predetermined range of mass-to-charge ratios, and
$m_{max}$ is an upper bound of the predetermined range of mass-to-charge ratios,
wherein the list of peaks identifies at most one peak in each interval, so as to obtain a vector for each of said at least one mass spectrum,
wherein the vector(s) for the at least one mass spectrum form a matrix representative of the microorganism; and
   (iii) providing an identification decision for the microorganism to be identified by comparing the representative matrix with a knowledge base of matrices representative of previously-identified microorganisms and/or types of microorganisms, wherein said knowledge base is stored in a memory.

12. The device of claim 11, wherein the predetermined range of mass-to-charge ratios is in the range from 3,000 Thomsons to 17,000 Thomsons.

13. The device of claim 11, wherein there are from 900 to 1,500 intervals.

14. The device of claim 13, wherein there are from 1,200 to 1,400 intervals.

15. The device of claim 11, wherein the peak kept in an interval of the subdivision is a maximum peak.

16. The device of claim 11, wherein the at least one mass spectrum of the sample of the microorganism was generated using MALDI-TOF spectrometry.

17. The device of claim 11, wherein the device further returns an identification decision to a user.

18. The device of claim 11, further comprising a mass spectrometer, wherein the at least one mass spectrum of the microorganism to be identified is generated by the mass spectrometer.

19. The device of claim 11, wherein the matrix representative of the microorganism to be identified is stored in the memory of the calculation unit.

20. The device of claim 11, wherein the matrix representative of the microorganism to be identified is in the form of a binarized matrix that identifies for each of the at least one mass spectrum the presence or absence of a peak in the intervals.

* * * * *